United States Patent [19]

Rich

[11] Patent Number: 4,604,477

[45] Date of Patent: Aug. 5, 1986

[54] METHOD FOR MAKING SILYLAROYLHALIDES AND REACTION PRODUCTS

[75] Inventor: Jonathan D. Rich, Ballston Lake, N.Y.

[73] Assignee: General Electric Company, Schenectady, N.Y.

[21] Appl. No.: 718,039

[22] Filed: Mar. 29, 1985

[51] Int. Cl.$^4$ .............................. C07F 7/08; C07F 7/18
[52] U.S. Cl. .................................. 556/436; 556/438; 556/439; 556/468
[58] Field of Search ................ 556/436, 468, 438, 439

[56] References Cited

U.S. PATENT DOCUMENTS 2,647,137  7/1953  Frisch et al. ................... 556/436 X
2,837,552  6/1958  George et al. ................... 556/468 X
4,363,925 12/1982  Acker et al. ..................... 556/468 X

OTHER PUBLICATIONS

"Chemical Abstracts", 60, p. P6868g, 12042f, 14534e, 1964.

*Primary Examiner*—Paul F. Shaver
*Attorney, Agent, or Firm*—William A. Teoli; James C. Davis, Jr.; James Magee, Jr.

[57] ABSTRACT

A method is provided for making silylaroylhalides such as chlorodimethylsilylbenzoyl chloride. Reaction is effected between substantially equivalent amounts of a polyhaloacyl aromatic compound, for example, terephthaloyl chloride and a polyhalopolysilane such as dichlorodisilane in the presence of a palladium catalyst.

10 Claims, No Drawings

METHOD FOR MAKING SILYLAROYLHALIDES AND REACTION PRODUCTS

CROSS REFERENCE TO RELATED APPLICATIONS

Reference is made to my copending application Ser. No. 647,332, for Silylation Method, filed Sept. 4, 1984 and copending application Ser. No. 718,039 filed 3/29/85, for Organopolysiloxane-Polyamide Block Copolymers and Method for Making, filed concurrently herewith, where the aforementioned applications are assigned to the same assignee as the present invention and incorporated herein by reference.

BACKGROUND OF THE INVENTION

As shown in my copending application Ser. No. 647,332, halogenated polysilanes, such as 1,2-dichlorotetramethyldisilane, can provide 1,4-(bis-chlorodimethylsilyl)benzene by reaction with terephthaloylchloride in the presence of a palladium catalyst. I discovered that a decarbonylation reaction occurred resulting in the production of product free of aromatic silyl ketone.

The present invention is based on my discovery that if terephthaloylchloride is reacted with substantially an equivalent amount of 1,2-dichlorotetramethyldisilane in the presence of palladium catalyst, para-chlorodimethylsilylbenzoylchloride is obtained as the exclusive silylaryl reaction product. This result is quite surprising since on a purely statistical basis, the aforementioned reaction of equivalent amounts of 1,2-dichlorotetramethyldisilane and terephthaloylchloride can result in a mixture of about 25 mole percent of terephthaloylchloride, 50 mole percent of para-chlorodimethylsilylbenzoylchloride and about 25 mole percent of 1,4-bis(-chlorodimethylsilyl)benzene.

STATEMENT OF THE INVENTION

There is provided by the present invention, a method for making halosilylaroylhalide which comprises, (1) effecting reaction between substantially equivalent amounts of aromatic polyacyl halide and organic halopolysilane having halogen radicals attached to silicon in the presence of an effective amount of a transition metal catalyst, (2) thereafter recovering silylaroylhalide from the mixture of (1).

Aromatic polyacylhalide which can be used in the practice of the present invention to make silylaroylhalide are, for example, terephthaloylchloride, isophthaloylchloride, phthaloylchloride, diphenic acid dichloride.

Among the halopolysilanes which can be used in the practice of the present invention, are for example, chloropentamethyldisilane, 1,2-dichlorotetramethyldisilane, 1,1-dichlorotetramethyldisilane, 1,1,2-trimethyltrichlorodisilane, 1,1,2,2-tetrachlorodimethyldisilane, hexachlorodisilane, 1,2-dibromotetramethyldisilane, 1,2-difluorotetramethyldisilane, 1,1,2,2,4,4,5,5-octamethyl-1,2,4,5-tetrasilacyclohexasiloxane, 1-chlorononamethyltetrasil-3-oxane, etc.

Among the transition metal catalysts which can be utilized in the practice of the present invention, there are included bisbenzonitrilepalladiumdichloride, bisacetonitrilepalladium dichloride, allylpalladiumchloride dimer, bis(triphenylphosphine)palladium dibromide, bis(triphenylphosphine)palladiumiodide, palladium on carbon, palladium on silica. Additional complexes of the following metals also can be used such as complexes of rhodium, iridium, cobalt, platinum and other Group VIII metals.

In preparing the halosilylaroyl halide, substantially equivalent amounts of the aromatic polyacylhalide and organic halopolysilane are heated at a temperature in the range of about 110° C. to about 300° C. in the presence of an effective amount of transition metal catalyst. An effective amount of catalyst is 0.001 to 0.1 parts of catalyst, per part of the reaction mixture.

It is preferred to conduct the reaction in an inert atmosphere such as under nitrogen. The halosilylaroylhalide can be recovered by fractional distillation of the mixture.

In addition to halosilylaroylhalide, the present invention is also directed to methods for making reaction products of such halosilylaroylhalide. It has been found, for example, the haloaryltetraorganodisiloxane can be made by effecting reaction between ½ mole of water per mole of halosilylaroylhalide, as shown by the following equation:

where X is a halogen, R is selected from halogen, monovalent $C_{(1-13)}$ hydrocarbon radicals and substituted $C_{(1-13)}$ monovalent hydrocarbon radicals and $R^1$ is selected from $C_{(6-13)}$ divalent aromatic radicals.

Radicals included within R are, for example, chloro, $C_{(1-8)}$ alkyl such as methyl, ethyl, propyl, butyl, haloalkyl, such as chloroethyl; $C_{(6-13)}$ aryl such as phenyl, tolyl, xylyl and halogenated aryl, for example, chlorophenyl. Radicals included within $R^1$ are, for example, phenylene, tolylene, xylylene and naphthalene. X radicals are, for example, chloro, bromo and fluoro.

In addition to the above shown disiloxane, the corresponding haloaroyl terminated polydiorganosiloxane having from about 7 to about 2000 chemically combined diorganosiloxy units can be made by effecting reaction between silanol terminated polydiorganosiloxane and the halosilylaroylhalide. Sufficient halosilylaroylhalide is utilized to provide for substantially equivalent amounts of halogen attached to silicon of the halosilylaroylhalide halide and silanol of the silanol terminated polydiorganosiloxane as shown as follows:

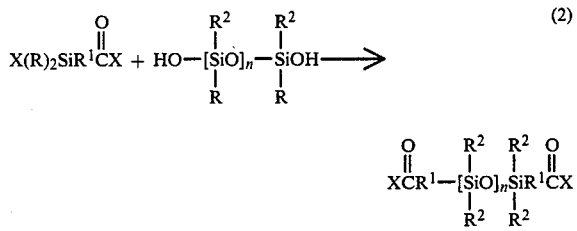

where R, $R^1$ and X are as previously defined, $R^2$ is selected from $C_{(1-13)}$ monovalent hydrocarbon radicals and substituted $C_{(1-13)}$ monovalent hydrocarbon radicals and n is an integer having a value of 7 to 2000 inclusive.

It also has been found that introduction of the halosilylaroylhalide to an excess of aqueous alkanol, such as methanol, can provide the corresponding bisarylolester tetraorganodisiloxane in quantitative yields as shown by the following equation:

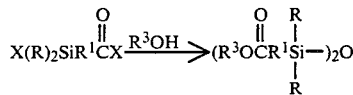 (2)

where R, $R^1$ and X are as previously defined and $R^3$ is a $C_{(1-8)}$ alkyl radical.

If desired, the corresponding alkylesteraroyl terminated polydiorganosiloxane can be made by standard equilibration techniques utilizing the above bis(tetraorgano disiloxane) bis(aroyl ester) with cyclo octaorganotetrasiloxane in the presence of an acid catalyst at elevated temperatures.

In order that those skilled in the art will be better able to practice the present invention, the following examples are given by way of illustration and not by way of limitation. All parts are by weight.

EXAMPLE 1

A neat mixture of 45.3 grams (0.22 mole) of terephthaloylchloride and 51 grams (0.26 moles, having a 94% purity) of 1,2-dichlorotetramethyldisilane were stirred under nitrogen and heated to 140° to produce a homogeneous solution. There was added to the mixture 100 mg of bis(benzonitrile)palladiumchloride and 220 mg of triphenylphosphine while the mixture was stirred. Carbon monoxide was immediately evolved from the mixture and was monitored by water displacement over a reaction period of 12 hours at 140° C. After two hours dimethyldichlorosilane was continuously distilled from the reaction mixture. The reaction mixture was then fractionally distilled to provide 38 grams or a 73% yield of para-chlorodimethylsilylbenzoylchloride as a clear liquid. It had a boiling point of 89° C./0.1 torr. Its identity was further confirmed by NMR and IR.

EXAMPLE 2

A solution of 3 gms ($1.29 \times 10^{-3}$ moles) of 4-chlorodimethylsilylbenzoyl chloride in 50 ml of reagent grade methanol (2-5% water) was stirred at room temperature for two hours. An exothermic reaction occurred. The methanol solvent was removed in vacuo leaving an oily solid. The solid was recrystallized from pentane. There was obtained 2.52 gms, or a 97% yield of a needle-like colorless product having a m.p. of 60°-61.5° C. Based on method of preparation, the product was 1,3-bis(p-methylbenzoate)tetramethyldisiloxane. Its identity was confirmed by its NMR and IR spectra.

A 50 ml toluene solution of 5.52 grams ($1.87 \times 10^{-2}$ moles) of octamethylcyclotetrasiloxane was heated to reflux. After 7 ml of the solvent was removed to effect the drying of the cyclic siloxane, the solution was cooled to 67° C. and 0.75 gram ($1.87 \times 10^{-3}$ moles) of 1,3-bis(p-methylbenzoate)tetramethyldisiloxane, 5 microliters of triflic anhydride and 1 microliter of water were introduced into the mixture. The mixture was then heated to 67° C. for 10 hours. After the mixture had cooled to room temperature there was added 75 ml of methylene chloride and 300 mg of anhydrous magnesium oxide which was introduced to neutralize the solution. The solution was then decolorized with carbon black, filtered and solvent removed in vacuo. The resulting crude product was heated 100° C. under 0.01 torr for 6 hours to remove volatile siloxane products. Cooling of the product provided 2.7 grams (43% yield) of product. Based on method of preparation and its NMR, the product was a clear viscous polydimethylsiloxane having an average of 29 dimethylsiloxy units and end-capped with methylbenzoate. Its identity was further confirmed by IR.

EXAMPLE 3

There was added at room temperature, a solution of 45 grams of a silanol terminated polydimethylsiloxane having an average of about 500 chemically combined dimethylsiloxy units dissolved in 150 ml of dry toluene to 40 grams of p-chlorodimethylsilylbenzoyl chloride. A constant vacuum of 20 torr was maintained to facilitate removal of HCl gas. Upon completion of the addition, a mixture which had been stirring, was stirred for an additional two hours to insure complete reaction. The toluene was then removed by evaporation from the mixture. There was obtained a two phase mixture consisting of a silicone fluid and excess chlorosilane. The chlorosilane was removed and the remaining material was heated to 120° C. at 0.1 torr. Based on method of preparation, there was obtained a polydimethylsiloxane having the formula,

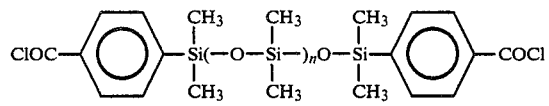

where n is equal to about 500. Its identity was further confirmed by IR and proton NMR.

The same procedure was repeated, except that there was utilized a silanol terminated polydimethylsiloxane having an average of about 165 chemically combined dimethylsiloxy units and initial viscosity at 2880 cps. Polydimethylsiloxane polymer was obtained having the formula

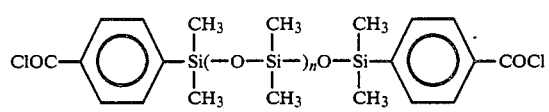

where n is equal to about 165. Its identity was further confirmed by NMR and IR and its final solution viscosity was 2920 cps.

There was stirred rapidly a solution of 5.85 grams (0.05 m) of N',N-diethylenediamine and 10.6 grams (0.1 m) of sodium carbonate and 250 ml of water. There was added to this solution, a solution containing 6.5 grams of benzoyl chloride end-capped polydimethylsiloxane fluid having an average of about 165 polydimethylsiloxy units dissolved in 50 ml of dry chloroform. The resulting mixture was stirred for 45 seconds. There was then added to the resulting mixture an 80 ml chloroform solution containing 10.1 grams of terephthaloylchloride which was rapidly introduced and the resulting mixture was stirred for 10 minutes at high speed. The mixture was then allowed to settle resulting in two phases. The organic phase was separated and the solvent was removed to produce 8.3 grams of a white solid or 43% of isolated yield. The produce was found to be soluble in chloroform and methylene chloride. Based on method of preparation, the produce was a polydimethylsiloxane polyamide block polymer consisting essentially of polydimethylsiloxane blocks chemically combined to amide or polyamide blocks.

The identity of the block polymer was further confirmed by IR analysis. The 20% methylene chloride solution was cast into a 10 micron film which was found to be a transparent, tough rubber material.

EXAMPLE 4

A mixture of 5.0 gm ($2.46 \times 10^{-3}$ moles) of isophthaloylchloride and 7.5 gm of 95% purity 1.2 dichlorotetramethyldisilane ($3.7 \times 10^{-3}$) was heated neat to 150° C. under an atmosphere of nitrogen. There was added 1.0 gm (0.4 mole %) of 1% palladium on carbon 30 mesh resulting in gaseous evolution of carbon monoxide. After 15 hours of reaction at 150° C., the mixture was cooled to room temperature. Gas chromatographic analysis of the crude mixture confirmed formation of only one aroylchloride. The catalyst was filtered, washed with 75 ml of dry dichloromethane and the combined filtrate was rotary evaporated to remove volatile solvent. Vacuum distillation of the remaining material gave 3.50 gm (61% isolated yield) of 3-chlorodimethylsilylbenzoylchloride as a clear liquid b.p. 98° C./0.1 torr. No disilylated product was observed. The identity of the 3-chlorodimethylsilylbenzoylchloride was confirmed by IR and NMR analysis.

Although the above examples are directed to only a few of the very variables which can be used in the practice of the methods of the present invention, it should be understood that the present invention provides a much broader variety of silylaroylhalides, the corresponding organo siloxanes end-capped with haloaroyl groups and the corresponding esters thereof, as shown in the description preceding these examples.

What I claim as new and desire to secure by Letters Patent of the United States is:

1. A method for making halosilylaroylhalide which comprises,
    (A) effecting reaction between substantially equivalent amounts of an aromatic polyacyl halide and an organic halopolysilane having halogen radicals attached to silicon in the presence of an effective amount of a transition metal catalyst,
    (B) thereafter recovering silylaroylhalide from the mixture of (1).
2. A method for making para-chlorodimethylsilylbenzoylchloride in accordance with claim 1.
3. A method in accordance with claim 1, where the aromatic polyacylhalide is terephthaloylchloride.
4. A method in accordance with claim 1, where the aromatic polyacylhalide is isophthaloylchloride.
5. A method in accordance with claim 1, where the halopolysilane is 1,2-dichlorotetramethyldisilane.
6. A method which comprises effecting reaction between a halosilylaroylhalide and an aqueous alkanol solution, where there is used more than 1 mole of alkanol per mole of halosilylaroylhalide.
7. A method for making a tetraorganodisiloxane bisaroylester in accordance with claim 6.
8. A method for making 1,3-bis(p-methylbenzoate)-tetramethyldisiloxane in accordance with claim 6.
9. A method for making an aroylhalide terminated polydiorganosiloxane which comprises effecting reaction between halosilylaroylhalide and silanol terminated polydiorganosiloxane.
10. Halosilylaroyl terminated polydiorganosiloxane having from about 7 to about 2000 chemically combined diorganosiloxy units.

* * * * *